US00PP28963P3

(12) United States Plant Patent
Madsen

(10) Patent No.: US PP28,963 P3
(45) Date of Patent: Feb. 13, 2018

(54) ***CAMPANULA* PLANT NAMED 'PKM04'**

(50) Latin Name: ***Campanula* hybrid**
Varietal Denomination: PKM04

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 44 days.

(21) Appl. No.: 14/756,950

(22) Filed: Nov. 2, 2015

(65) Prior Publication Data

US 2017/0127597 P1 May 4, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from PLUTO Plant Variety Database for corresponding Canadian application No. 15-8740 filed Nov. 3, 2015 (1 page) (http://www.wipo.int/pluto).
Printout of application information from PLUTO Plant Variety Database for corresponding CPVO application No. 2015/2215 filed Sep. 23, 2015 (1 page) (http://www.wipo.int/pluto).

*Primary Examiner* — Keith O. Robinson
(74) *Attorney, Agent, or Firm* — Foley & Lardner LLP

(57) ABSTRACT

A distinct cultivar of *Campanula* plant named 'PKM04' characterized by its upright, freely branching and compact growth habit and bicolored (white/violet) broad campanulate flowers.

3 Drawing Sheets

Latin name of genus and species of the plant claimed: *Campanula* hybrid.

Variety denomination: 'PKM04'.

BACKGROUND OF THE INVENTION

The present invention relates to a new and distinct cultivar of *Campanula* plant, botanically known as *Campanula* hybrid, common name Bellflower and hereinafter referred to by the name 'PKM04'.

The new *Campanula* originated from a planned cross between two different *Campanula* species; the female parent being an unnamed, proprietary *Campanula* variety (unpatented) and the male parent being an unnamed, proprietary *Campanula* variety (unpatented). The initial crossing was performed in 2012 by the Inventor, followed by further testing and selection in 2013 after vegetative propagation.

Vegetative propagation was performed by terminal cuttings taken and propagated in Søhus, Denmark. Asexual reproduction of the new *Campanula* cultivar by terminal cuttings has demonstrated that the combination of characteristics as herein disclosed for the new cultivar are firmly fixed and retained through successive generations of asexual reproduction. The new cultivar asexually reproduces true-to-type.

SUMMARY OF THE INVENTION

The following traits have been repeatedly observed and are determined to be the unique characteristics of 'PKM04'. These characteristics in combination distinguish 'PKM04' as a new and distinct cultivar:

1. Upright and freely branching growth habit;
2. Bicolored flowers.
3. Compact growth with no need for growth regulators Plants of the cultivar 'PKM04' can be compared to plants of the *Campanula* 'PKM03' (U.S. Plant Pat. No. 27,516). In side-by-side comparisons conducted by the Inventor in Søhus, Denmark, 'PKM04' and 'PKM03' differ in the following characteristics:

1. 'PKM04' produce smaller plants than 'PKM03'.
2. 'PKM04' has darker purple flowers than 'PKM03'.
3. 'PKM04' has darker green leaves than 'PKM03'
4. 'PKM04' has much less pollen than 'PKM03', thus the purple styles are visible whereas the styles of 'PKM03' are covered with yellowish pollen.

Data on plants of the parent varieties is no longer available for comparison with plants of the new cultivar *Campanula* 'PKM04'.

BRIEF DESCRIPTION OF THE PHOTOGRAPHS

The accompanying colored photographs illustrate the overall appearance of the new *Campanula* 'PKM04', showing the colors as true as it is reasonably possible to obtain in colored reproductions of this type. Colors in the photographs may differ slightly from the color values cited in the detailed botanical description, which more accurately describe the actual colors of 'PKM04'. Plants in the photographs are shown approximately 14 weeks after propagation.

Figure 1:
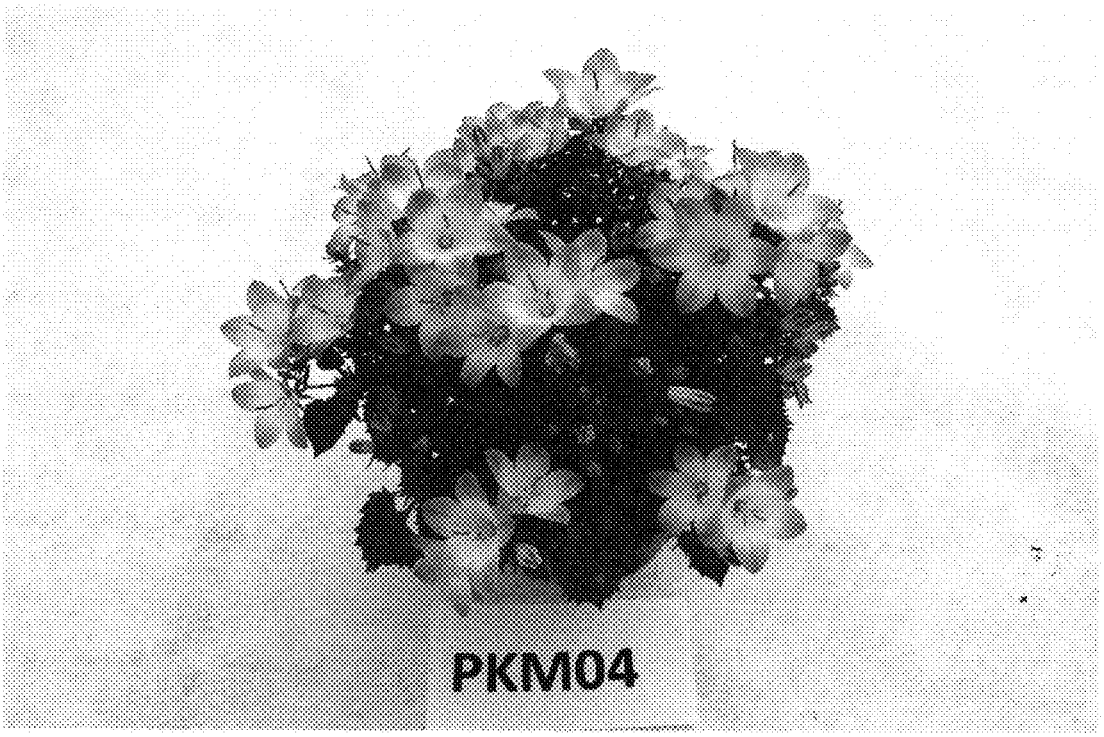

FIG. 1: The photograph comprises a side perspective view of a typical flowering plant of 'PKM04', as grown in a 10.5 cm pot.

Figure 2:
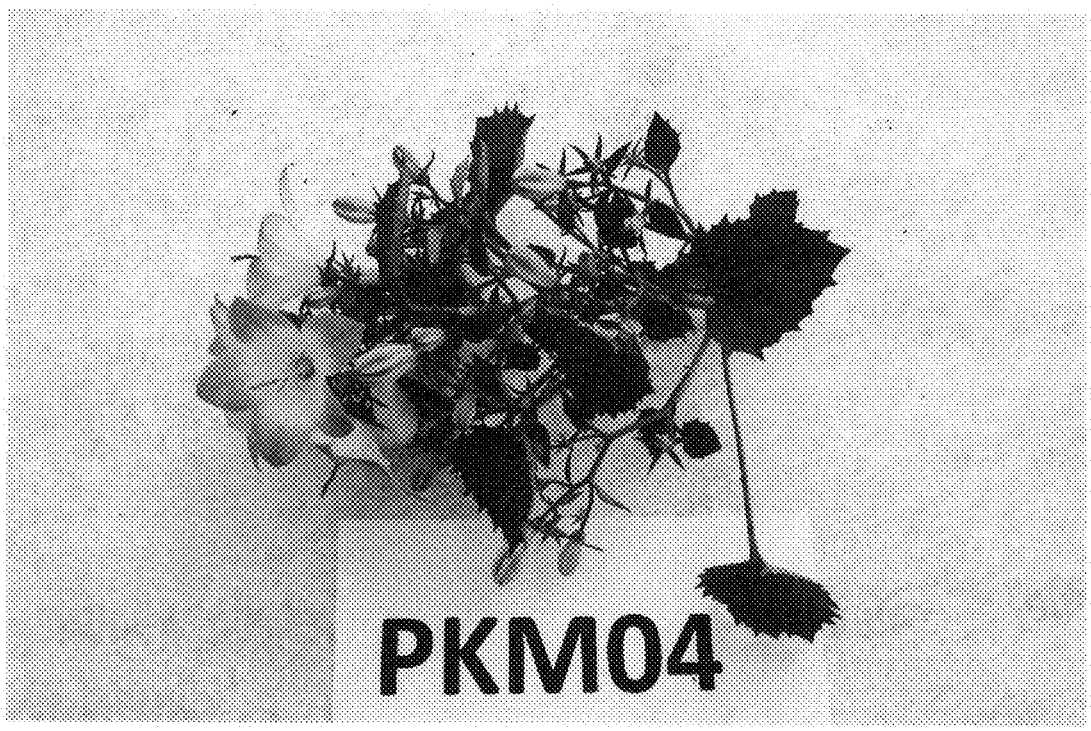

FIG. 2: The photograph comprises a close-up view of a typical inflorescence of 'PKM04'.

Figure 3:
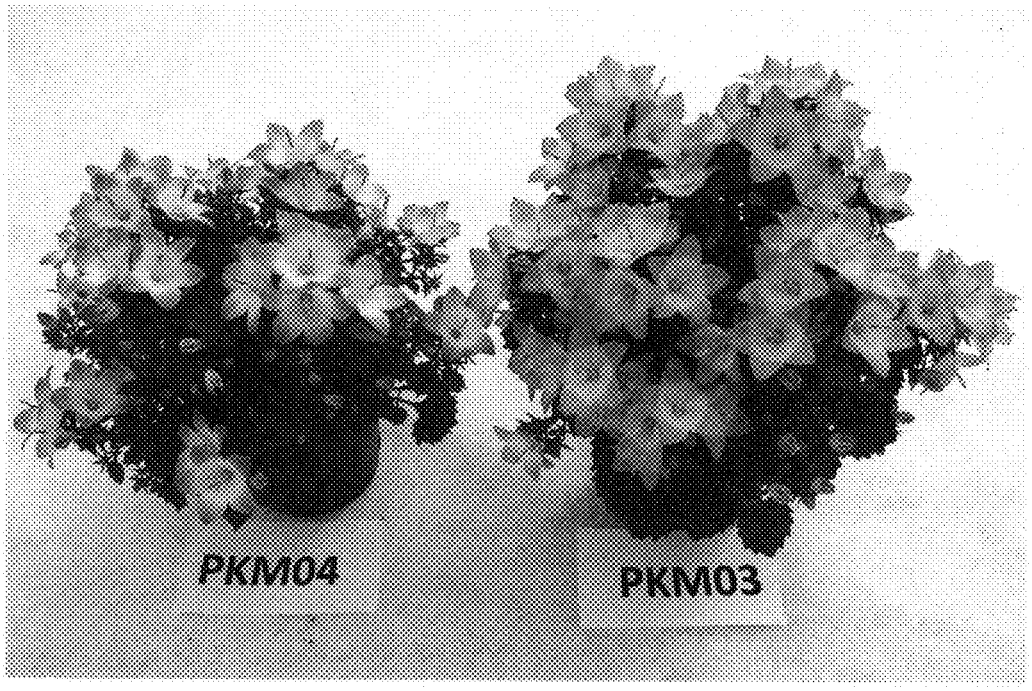

FIG. 3: The photograph comprises a side perspective view of typical flowering plants of 'PKM04' and 'PKM03', as grown in a 10.5 cm pot.

DETAILED BOTANICAL DESCRIPTION

The new *Campanula* 'PKM04' has not been observed under all possible environmental conditions. The phenotype of the new cultivar may vary with variations in environment such as temperature, light intensity, day length, growth regulator treatment and fertility level without any variance in genotype.

The aforementioned photographs, together with the following observations, measurements and values describe plants of the new *Campanula* 'PKM04' as grown under greenhouse conditions in a 10.5 cm pot.

The age of the 'PKM04' plants described is about 14 weeks after propagation. Color references are made to The Royal Horticultural Society Colour Chart (R.H.S.), 5$^{th}$ edition, 2007, except where general colors of ordinary significance are used.

Classification:

*Botanical.*—*Campanula* hybrid.

Parentage:

*Female or seed parent.*—Unnamed proprietary variety of *Campanula* (unpatented).

*Male or pollen parent.*—Unnamed proprietary variety of *Campanula* (unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Upright growth habit and overall globular shape. Freely branching with basal shoots. No pinching required.

*Crop time.*—After rooting, about 14 weeks are required to produce finished flowering plants in up to 11 cm pots.

*Plant height (from soil level to top of plant plane).*—Up to 15 cm.

*Plant spread (width).*—Up to 24 cm.

*Vigor.*—Good. Average growth rate.

*Lateral branches.*—Number per plant: 10-15. Length: up to 14 cm (including flowers). Diameter: approximately 3 mm. Internode length: 5-15 mm.

*Stem.*—Shape: Round-edged. Strength: Stiff. Color: Green, RHS 137B, as leaf blade. Pubescence: None. Lactate: a limited quantity of white, RHS NN155D, lactate is produced.

Foliage description:

*Quantity per lateral branch.*—5-10.

*Leaf arrangement.*—Single, alternate.

*Leaf shape.*—Basal: Cordate. Apical: Elliptic to ovate.

*Leaf tip.*—Acute (Apical and Basal leaves).

*Leaf base.*—Basal: Cordate. Apical: Acute to Obtuse.

*Leaf length.*—Basal: up to 30 mm. Apical: 10-15 mm.

*Leaf width.*—Basal: up to 30 mm. Apical: 10 mm.

*Pubescence.*—None.

*Margin.*—Dentate to Serrate, more prominent on basal than apical leaves.

*Color.*—Upper Surface, RHS N137A, Green. Lower Surface, RHS 138B, Green.

*Variegation.*—Absent.

*Venation.*—Pattern: Pinnipalmate. Color: Upper Surface: same as leaf blade, green RHS N137A. Lower Surface: same as blade, green RHS 138B.

*Petiole.*—Length: Basal: up to 50 mm. Apical: 0-10 mm. Diameter: 1-2 mm. Color: same as leaf blade, green RHS N137A.

Inflorescence description:

*Flower arrangement and shape.*—Broad campanulate flowers. Upright to spreading arrangement. Inflorescences are panicles.

*Flower longevity.*—Longevity of individual flowers is highly dependent on temperature and light conditions; average about 2-3 weeks. Flowers persistent. Natural flowering season spring to early summer.

*Inflorescence size.*—Length: up to 10 cm.

*Flowers.*—Quantity per inflorescence: 12-16. Length: about 20 mm. Diameter: 30-40 mm. Arrangement and Shape: Single, sympetalous, campanulate. Upright to outward facing. Petal Color: Inner surface: Base: NN155B , White. Apex: RHS 88B, Violet. Outer surface: Base: RHS NN155B. Apex: RHS 91B. Little darker/more intense at the apex than at the base. Color does not fade.

*Corolla.*—Curvature: weakly to moderately reflexing when fully open. Petal number: 5, fused at lower half. Petal Shape: Obtuse lobes. Petal Margin: Entire. Petal Apex: Acute. Lobe Length: up to 13 mm lobes. Lobe Width: 10-13 mm maximum on lobes. Petal texture: Glabrous on both upper and lower surfaces. Fragrance: None. Petaloid lobes: Absent.

*Sepals.*—Arrangement: Free. Appearance: Glabrous. Quantity per flower: 5. Length: 5-8 mm. Width: 2 mm. Overall shape: Deltoid. Apex: Acute. Margin: Entire. Color (mature and immature): Upper and lower surfaces: Green, as leaf blade, RHS N137A. Pedicel: Length: 5-10 mm. Diameter: About 1 mm. Color: Green, as leaf blade, RHS N137A.

*Buds.*—Length: Up to 15 mm. Diameter: Up to 7 mm. Shape: Oblong, ridged. Color: Changes from yellow-green to nearly 88B at the apex. Coloration of buds starts at the tip.

Reproductive organs:

*Pistil.*—Quantity: 1. Length: 15-20 mm.

*Style.*—Length: 12-18 mm. Color: almost white (RHS NN155D) at base (lower half), darker purple (RHS 94A) than petal upper part in the upper half.

*Ovary.*—Color: Green, RHS N137A.

*Stigma.*—Shape: Tripartite. Color: Greyish, area too small to determine R.H.S. value.

*Stamen.*—Number: 5.

*Anther.*—Size: 5 mm. Color: yellow to light brown, area too small to determine R.H.S. value.

*Pollen.*—Amount: None to very little. Color: Pale yellow; amount too small to determine R.H.S. value.

High/low temperature tolerance: Plant is not frost tolerant.

Disease resistance and/or susceptibility: Not tested.

I claim:

1. A new and distinct cultivar of *Campanula* hybrid plant named 'PKM04', as illustrated and described herein.

* * * * *